United States Patent [19]

Maraganore et al.

[11] Patent Number: 5,514,409
[45] Date of Patent: May 7, 1996

[54] METHODS FOR COATING INVASIVE DEVICES WITH INHIBITORS OF THROMBIN

[75] Inventors: John M. Maraganore, Concord; Paul R. Bourdon, Sommerville; Jo-Ann M. Jablonski, Middleborough, all of Mass.

[73] Assignee: Biogen, Inc., Cambridge, Mass.

[21] Appl. No.: 431,678

[22] Filed: May 2, 1995

Related U.S. Application Data

[62] Division of Ser. No. 924,549, Jul. 31, 1992, Pat. No. 5,425,936, which is a division of Ser. No. 652,929, Feb. 8, 1991, Pat. No. 5,240,913, which is a continuation-in-part of Ser. No. 549,388, Jul. 6, 1990, Pat. No. 5,196,404, which is a continuation-in-part of Ser. No. 395,482, Aug. 18, 1989, abandoned.

[51] Int. Cl.$^6$ .................................................. A01N 1/02
[52] U.S. Cl. .................. 427/2.24; 424/1.69; 427/2.3; 514/18; 530/330
[58] Field of Search .................. 424/1.69; 427/2.24, 427/2.3; 514/18; 530/330

[56] References Cited

U.S. PATENT DOCUMENTS

| | | | |
|---|---|---|---|
| 4,971,953 | 11/1990 | Krstenansky | 514/14 |
| 5,240,913 | 8/1993 | Maraganore et al. | 514/13 |
| 5,425,936 | 6/1995 | Maraganore et al. | 424/1.69 |

*Primary Examiner*—Michael Lusignan
*Attorney, Agent, or Firm*—Fish & Neave; James F. Haley, Jr.; Andrew S. Marks

[57] ABSTRACT

This invention relates to coating invasive devies with novel biologically active molecules which bind to and inhibit thrombin. These molecules comprise a catalytic site directed moiety (CSDM) of the formula:

$$X-R_2-R_3-R_4-R_5-R_6-Y$$
$$|$$
$$R_1$$

wherein X is hydrogen or is characterized by a backbone chain consisting of from 1 to 100 atoms; $R_1$ is selected from the group consisting of unsubstituted, mono-substituted, di-substituted and tri-substituted saturated ring structures; $R_2$ is a bond or is characterized by a backbone chain consisting of from 1 to 5 atoms; $R_3$ is a bond or is characterized by a backbone chain consisting of from 1 to 3 atoms; $R_4$ is any amino acid; $R_5$ is any L-amino acid which comprises a guanidinium- or amino-containing side chain group; $R_6$ is a non-amide bond; and Y is characterized by a backbone chain consisting of from 1 to 9 atoms; or the formula:

$$X-R_2-R_3-R'_4-R_5-R_6-Y$$
$$|$$
$$R'_1$$

wherein $R'_1$ is selected from the group consisting of unsubstituted, mono-substituted, di-substituted and tri-substituted ring structures; $R'_4$ is any amino acid comprising a side chain group characterized by the capacity to accept a hydrogen bond at a pH of between about 5.5 and 9.5; and X, $R_2$, $R_3$, $R_5$, $R_6$ and Y are defined as above. Preferred thrombin inhibitors are further characterized by a anion binding exosite associating domain (ABEAM) and a linker portion of between 18 Å and 42 Å in length which connects the Y to the ABEAM.

11 Claims, 3 Drawing Sheets

METHODS FOR COATING INVASIVE DEVICES WITH INHIBITORS OF THROMBIN

CROSS-REFERENCE TO PRIOR APPLICATIONS

This application is a divisional of application Ser. No. 924,549, filed Jul. 31, 1992, now U.S. Pat. No. 5,425,936, is said Jun. 20, 1995 divisional of application Ser. No. 652, 929, filed Feb. 8, 1991, now U.S. Pat. 5,240,913, issued Aug. 31, 1993, which is a continuation-in-part of application Ser. No. 549,388, filed Jul. 6, 1990, now U.S. Pat. No. 5,196,404, issued Mar. 23, 1993, which is a continuation-in-part of application Ser. No. 395,482, filed Aug. 18, 1989, now abandoned.

TECHNICAL FIELD OF INVENTION

This invention relates to coating invasive devies with novel biologically active molecules which bind to and inhibit thrombin. These molecules comprise a catalytic site directed moiety (CSDM) of the formula:

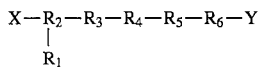

wherein X is hydrogen or is characterized by a backbone chain consisting of from 1 to 100 atoms; $R_1$ is selected from the group consisting of unsubstituted, mono-substituted, di-substituted and tri-substituted saturated ring structures; $R_2$ is a bond or is characterized by a backbone chain consisting of from 1 to 5 atoms; $R_3$ is a bond or is characterized by a backbone chain consisting of from 1 to 3 atoms; $R_4$ is any amino acid; $R_5$ is any L-amino acid which comprises a guanidinium- or amino-containing side chain group; $R_6$ is a non-amide bond; and Y is a bond or is characterized by a backbone chain consisting of from 1 to 9 atoms; or the formula:

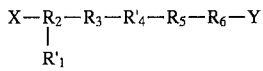

wherein $R_1'$ is selected from the group consisting of unsubstituted, mono-substituted, di-substituted and tri-substituted ring structures; $R_4'$ is any amino acid comprising a side chain group characterized by the capacity to accept a hydrogen bond at a pH of between about 5.5 and 9.5; and X, $R_2$, $R_3$, $R_5$, $R_6$ and Y are defined as above. Preferred thrombin inhibitors are further characterized by a anion binding exosite associating domain (ABEAM) and a linker portion of between 18Å and 42Å in length which connects Y to the ABEAM.

BACKGROUND ART

Acute vascular diseases, such as myocardial infarction, stroke, pulmonary embolism, deep vein thrombosis, peripheral arterial occlusion, and other blood system thromboses constitute major health risks. Such diseases are caused by either partial or total occlusion of a blood vessel by a blood clot, which contains fibrin and platelets.

Thrombin is the naturally occurring protein which catalyzes the conversion of fibrinogen to fibrin, the final step in blood clot formation. In addition to catalyzing the formation of a fibrin clot, thrombin also activates platelet aggregation and release reactions. This means that thrombin plays a central role in both acute platelet-dependent (arterial) thrombosis [S. R. Hanson and L. A. Harker, "Interruption of Acute Platelet-Dependent Thrombosis by the Synthetic Antithrombin D-Phenylalanyl-L-Prolyl-L-Arginylchloromethylketone", Proc. Natl. Acad. Sci. USA, 85, pp. 3184–88 (1988)] and fibrin-dependent (venous) thrombosis.

Thrombin has several other bioregulatory roles [J. W. Fenton, II, "Thrombin Bioregulatory Functions", Adv. Clin. Enzymol., 6, pp. 186–93 (19988)]. For example, thrombin can directly activate an inflammatory response by stimulating the synthesis of platelet activating factor (PAF) in endothelial cells [S. Prescott et al., "Human Endothelial Cells in Culture Produce Platelet-Activating Factor (1-alkyl-2-acetyl-sn-glycero-3-phosphocholine) When Stimulated With Thrombin", Proc. Natl. Acad. Sci. USA, 81, pp. 3534–38 (1984)]. PAF is exposed on the surface of endothelial cells and serves as a ligand for neutrophil adhesion and subsequent degranulation [G. M. Vercolletti et al., "Platelet-Activating Factor Primes Neutrophil Responses to Agonists: Role in Promoting Neutrophil-Mediated Endothelial Damage", Blood, 71, pp. 1100–07 (1988)]. Alternatively, thrombin may promote inflammation by increasing vascular permeability which can lead to edema [P. J. Del Vecchio et al., "Endothelial Monolayer Permeability To Macromolecules", Fed. Proc., 46, pp. 2511–15 (1987)]. Reagents which block the active site of thrombin, such as hirudin, interrupt the activation of platelets and endothelial cells [C. L. Knupp, "Effect of Thrombin Inhibitors on Thrombin-Induced Release and Aggregation", Thrombosis Res., 49, pp. 23–36 (1988)].

Thrombin has also been implicated in promoting cancer, based on the ability of its native digestion product, fibrin, to serve as a substrate for tumor growth [A. Falanga et al., "Isolation and Characterization of Cancer Procoagulant: A Cysteine Proteinase from Malignant Tissue", Biochemistry, 24, pp. 5558–67 (1995); S. G. Gordon et al., "Cysteine Proteinase Procoagulant From Amnion-Chorion", Blood, 66, pp. 1261–65(1995); and A. Falanga et al., "A New Procoagulant In Acute Leukemia", Blood, 71, pp. 870–75 (1988)]. And thrombin has been implicated in neurodegenerative diseases based on its ability to cause neurite retraction [D. Gurwitz et al., "Thrombin Modulates and Reverses Neuroblastoma Neurite Outgrowth", Proc. Natl. Acad. Sci. USA, 85, pp. 3440–44 (1988)]. Therefore, the ability to regulate the in vivo activity of thrombin has many important clinical implications.

One route to the successful treatment or prevention of acute vascular disease is the inhibition of thrombin. Many types of thrombin inhibitors are already known in the art. Heparin, an indirect inhibitor of thrombin, is widely used to treat venous thrombosis. Although effective against fibrindependent clot formation, heparin has little efficacy in inhibiting thrombin-induced activation of platelets. Therefore, this drug is not utilized in the treatment of arterial thromboses. Moreover, heparin produces many undesirable side effects, including hemorrhaging and thrombocytopenia.

Hirudin is a naturally occurring polypeptide which is produced by the blood sucking leech Hirudo medicinalis. This compound, which is synthesized in the salivary gland of the leech, is the most potent natural inhibitor of coagulation known. Hirudin prevents blood from coagulating by binding tightly to thrombin ($K_d$=2×10$^{-11}$) in a 1:1 stoichiometric complex [S. R. Stone and J. Hofsteenge, "Kinetics of the Inhibition of Thrombin by Hirudin", Biochemistry, 25, pp. 4622–28 (1986)]. This, in turn, inhibits thrombin from catalyzing the conversion of fibrinogen to fibrin (clot), as well as inhibiting all other thrombin-mediated processes [J.

W. Fenton, II, "Regulation of Thrombin Generation and Functions", *Semin. Thromb. Hemost.*, 14, pp. 234–40 (1988)].

Hirudin inhibits thrombin by binding to the latter at two separate sites. Initially, the C-terminus of hirudin interacts with an "anion-binding exosite" (ABE) in thrombin [J. W. Fenton, II et al., "Thrombin Anion Binding Exosite Interactions with Heparin and Various Polyanions", *Ann. New York Acad. Sci.*, 556, pp. 158–65 (1989)]. Following this low affinity binding, the hirudin-thrombin complex undergoes a conformational change and amino terminal portion of hirudin is able to bind to the catalytic site of thrombin [S. Kono et al., "Analysis of Secondary Structure of Hirudin and the Conformational Change Upon Interaction with Thrombin", *Arch. Biochem. Biophys.*, 267, pp. 158–66 (1988)].

The isolation, purification and amino acid sequence of hirudin are known in the art [P. Walsmann and F. Markwardt, "Biochemical and Pharmacological Aspects of the Thrombin Inhibitor Hirudin", *Pharmazie*, 36, pp. 653–60 (1981); J. Dodt et al., "The Complete Covalent Structure of Hirudin: Localization of the Disulfide Bonds", *Biol. Chem. Hoppe-Seyler*, 366, pp. 379–85 (1995); S. J. T. Mao et al., "Rapid Purification and Revised Amino Terminal Sequence of Hirudin: A Specific Thrombin Inhibitor of the BloodSucking Leech", *Anal. Biochem*, 161, pp. 514–18 (1987); and R. P. Harvey et al., "Cloning and Expression of a cDNA Coding for the Anti-Coagulant Hirudin from the Bloodsucking Leech, *Hirudo medicinalis*", *Proc. Natl. Acad. Sci. USA*, 83, pp. 1084–88 (1986)].

In animal studies, hirudin, purified from leeches, has demonstrated efficacy in preventing venous thrombosis, vascular shunt occlusion and thrombininduced disseminated intravascular coagulation. In addition, hirudin exhibits low toxicity and a very short clearance time from circulation [F. Markwardt et al., "Pharmacological Studies on the Antithrombotic Action of Hirudin in Experimental Animals", *Thromb. Haemost.*, 47, pp. 226–29 (1982)].

Hirudin has more recently been cloned and expressed in *E.coli* [European patent applications 58,564, 168,342 and 171,024] and yeast [European patent application 200,655]. Despite these advances, hirudin is still moderately expensive to produce and it is not widely available commercially.

Recently, efforts have been made to identify peptide fragments of native hirudin or derivatives thereof which are also effective in prolonging clotting times. Such compounds are described in European patent application Nos. 276,014, 291,982, 333,356, 341,607 and 372,670. The molecules described in these patent applications demonstrated varying efficacy in inhibiting clot formation, but were all 2 to 4 orders of magnitude less potent than hirudin. Such peptide fragments, therefore, may not be fully satisfactory to dissolve blood clots in on-going therapy regimens.

More recently, compounds which mimic the action of hirudin by binding to both the anion binding exosite and the catalytic site of thrombin have been described [U.S. Pat. No. 5,196,404]. These compounds demonstrate thrombin inhibitory activity equal to or greater than native hirudin. They are also smaller than hirudin and therefore less antigenic. These inhibitors are also produced synthetically, allowing for the production of commercially feasible quantities at reasonable costs.

Despite the developments to date, there is an ongoing need for even more potent thrombin inhibitors which can be produced inexpensively and in commercially feasible quantities. Such inhibitors would not only be effective in treating and preventing vascular disease, but may also be therapeutically useful in treating cancer, neurodegenerative disease and inflammation.

SUMMARY OF THE INVENTION

The present invention provides methods of coating invasive devices with molecules which are potent inhibitors of thrombin. These molecules have been designed based on the three-dimensional X-ray crystallographic structure of a thrombin-inhibitor complex. Because of this, the inhibitors of the present invention are spatially configured to provide the best fit into the three-dimensional spaces in and around the catalytic site of thrombin. This results in molecules which have optimal thrombin inhibitory activity.

The invention further provides coating invasive devices with thrombin inhibitors which additionally comprise a moiety that binds to the anion binding exosite of thrombin. These inhibitors qualitatively mimic the action of hirudin. Because these molecules are designed for optimal spatial configuration, they are more potent than hirudin. The high potency of the inhibitors of this invention allows them to be administered to patients in dosages which are comparatively lower than those required in hirudinbased therapy regimens.

Due to the fact that the molecules of the present invention may be prepared by chemical synthesis techniques, commercially feasible amounts may be produced inexpensively. Moreover, because the molecules of the present invention are significantly smaller than the thrombin inhibitors presently employed in medical treatment, they are less likely to stimulate an undesirable immune response in patients implanted with invasive devices coated with them. The molecules of the present invention may also be utilized in place of known thrombin inhibitors, especially heparin or hirudin.

As will be appreciated from the disclosure to follow, the inhibitors of this invention are useful in reducing the risk of thrombin-induced clot formation and/or platelet activation in patients receiving devices coated with them.

DETAILED DESCRIPTION OF THE INVENTION

Figure 1:
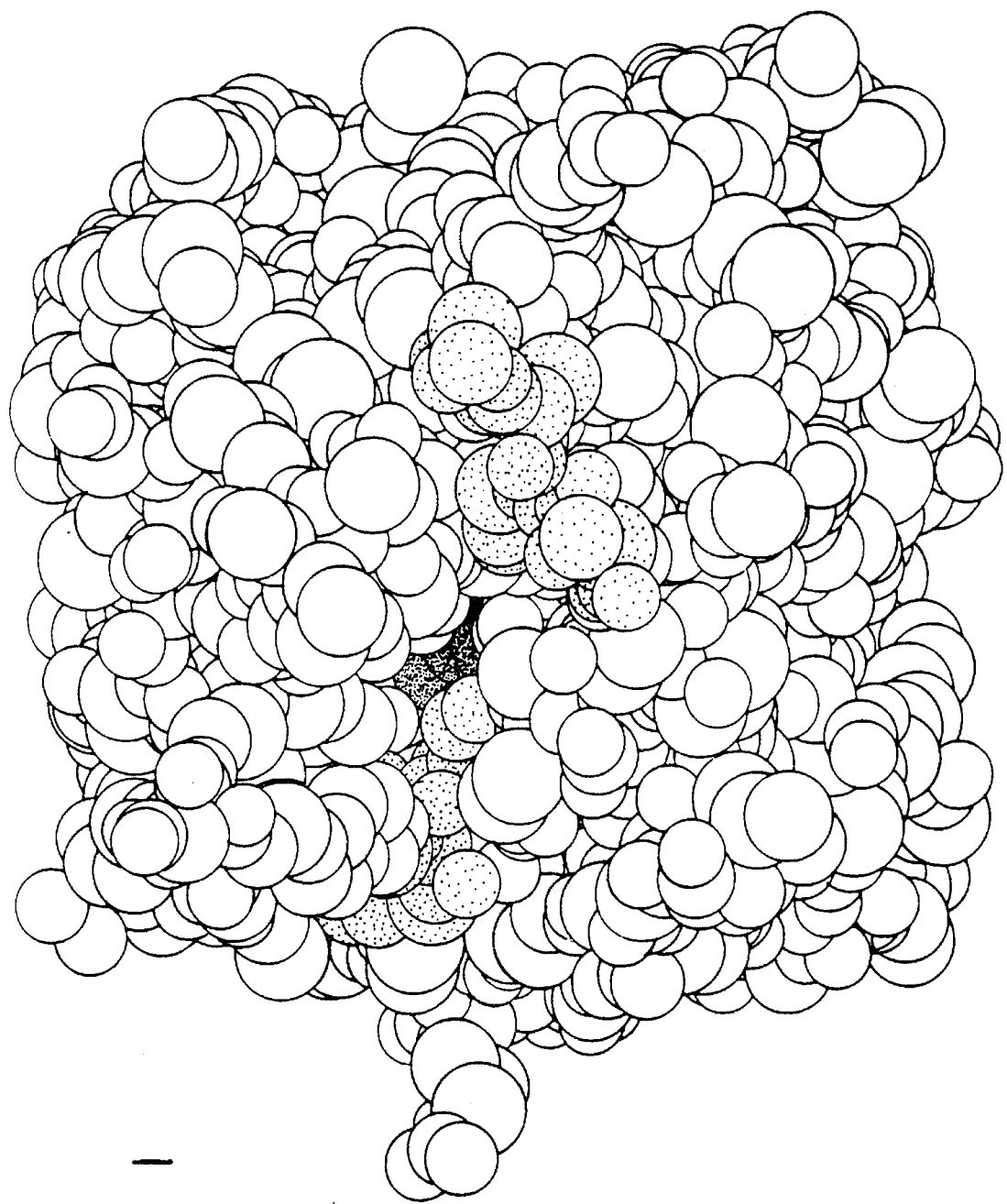
FIG. 1 depicts a space filling model of the Hirulog-8-thrombin complex.

The following common abbreviations of the amino acids are used throughout the specification and in the claims:

| | |
|---|---|
| Orn - ornithine | Gly - glycine |
| Ala - alanine | Val - valine |
| Leu - leucine | Ile - isoleucine |
| Pro - proline | Phe - phenylalanine |
| Trp - tryptophan | Met - methionine |
| Ser - serine | Thr - threonine |
| Cys - cysteine | Tyr - tyrosine |
| Asn - asparagine | Gln - glutamine |
| Asp - aspartic acid | Glu - glutamic acid |
| Lys - lysine | Arg - arginine |
| His - histidine | Nle - norleucine |
| Npa - napthylalanine | Cha - cyclohexylalanine |

| | |
|---|---|
| Hyp - hydroxyproline | TPro - thioproline |
| Ac - acetyl | Suc - succinyl |
| BOC - tertButoxycarbonyl | Tos - paraToluenesulfonyl |
| Cbz - Carbobenzyloxy | Inp - isonipecotic acid |
| 3,4,-dehydroPro - 3,4,-dehydroproline | Sar - sarcosine (N-methylglycine) |
| Tyr(OSO$_3$H) - tyrosine-O-sulfate | Tyr(SO$_3$H) - 3-sulfotyrosine |
| 3-,5-diiodoTyr - 3-,5-diiodotyrosine | |

The term "any amino acid" as used herein includes the L-isomers of the naturally occurring amino acids, as well as other "non-protein" α-amino acids commonly utilized by those in the peptide chemistry arts when preparing synthetic analogs of naturally occurring amino peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of "non-protein" α-amino acids include norleucine, norvaline, alloisoleucine, homoarginine, thioproline, dehydroproline, hydroxyproline (Hyp), isonipecotic acid (Inp), homoserine, cyclohexylglycine (Chg), α-amino-n-butyric acid (Aba), cyclohexylalanine (Cha), aminophenylbutyric acid (Pba), phenylalanines substituted at the ortho, meta, or para position of the phenyl moiety with one or two of the following: a ($C_1$–$C_4$) alkyl, a ($C_1$–$C_4$) alkoxy, halogen or nitro groups or substituted with a methylenedioxy group; β2- and 3-thienylal-alanine, β2- and 3-furanylalanine, β2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3- and 5-sulfo tyrosine, 3- and 5-carboxy-tyrosine, 3- and 5-phosphotyrosine, 4-methane sulfonic acid ester of tyrosine, 4-methane phosphonic acid ester of tyrosine, 4-phenylacetic acid, 3,5-diiodotyrosine, 3- and 5-nitrotyrosine, ε-alkyl lysine, delta-alkyl ornithine, and the D-isomers of any of the above amino acids. Unless specifically indicated, all amino acids referred to in this application are in the L-form.

The compounds referred to herein as tyrosine-O-sulfate, Tyr(OSO$_3$H) and O-sulfate ester of tyrosine are identical and have the structural formula:

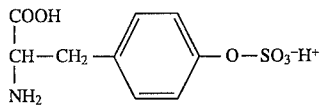

The compounds referred to herein as Tyr(SO$_3$H), 3-sulfotyrosine and 5-sulfo-tyrosine are identical and have the structural formula:

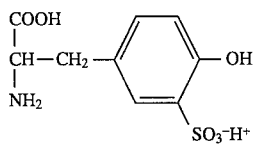

The term "patient" as used in this application refers to any mammal, especially humans.

The term "anionic amino acid" as used herein means a meta, para or ortho, mono- or di-substituted phenylalanine, cyclohexylalanine or tyrosine containing a negatively charged moiety, as well as S-alkylated cysteine, S-alkylated homocysteine, γ-carboxyglutamic acid, ε-alkyl lysine, delta-alkyl ornithine, glutamic acid, and aspartic acid. Examples of anionic amino acids are O-sulfate, O-phosphate and O-carboxylate esters of tyrosine, 3- and 5-sulfo-tyrosine, 3- and 5-carbo-tyrosine, 3- and 5-phospho- tyrosine, 4-methane sulfonic acid ester of tyrosine, 4-methane phosphonic acid ester of tyrosine, 4-phenylacetic acid, 3,5-diiodotyrosine and 3- and 5-nitrotyrosine.

The terms "catalytic site", "active site" and "active site pocket" as used herein, each refer to any or all of the following sites in thrombin: the substrate binding or "$S_1$" site; the hydrophobic binding or "oily" site; and the site where cleavage of a substrate is actually carried out ("charge relay site").

The term "backbone chain" as used herein, refers to the portion of a chemical structure that defines the smallest number of consecutive bonds that can be traced from one end of that chemical structure to the other. The atomic components that make up a backbone chain may comprise any atoms that are capable of forming bonds with at least two other atoms.

For example, each of the following chemical structures is characterized by a backbone chain of 7 atoms (the atoms which comprise the backbone chain are indicated in boldface):

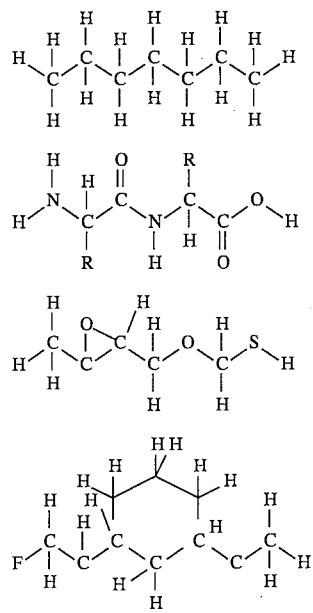

The term "calculated length" as used in this application, refers to a predicted measurement derived by summing up the bond lengths between the atoms that comprise the backbone chain. Bond lengths between any two given atoms are well known in the art [see, for example, *CRC Handbook of Chemistry and Physics*, 65th Edition, R. C. Weist, ed., CRC Press, Inc., Boca Raton, Fla. pp. F-166-70 (1984)].

Applicants have analyzed the structure of a thrombin-Hirulog-8 complex by three-dimensional X-ray crystallography. Hirulog-8 is an inhibitor that binds to both the anionic binding exosite and the catalytic site of thrombin. It has the formula: (D-Phe)-Pro-Arg-Pro-(Gly)$_4$-Asn-Gly-Asp-Phe-Glu-Glu-Ile-Pro-Glu-Glu- Tyr-Leu. The synthesis of this compound is described in Example 2 of this application. This crystallographic data revealed several structural features in and around the active site of thrombin that were crucial in designing the improved thrombin inhibitors of this invention.

One of these structural features is a hydrophobic pocket in thrombin adjacent to its catalytic center. In Hirulog-8, the N-terminal D-Phe residue, specifically the phenyl ring of that amino acid, occupies this space. Substituting a saturated ring for the unsaturated ring increases the lipophilic interactions with thrombin, thus increasing inhibitory potency. Therefore, according to one embodiment of this invention, the thrombin inhibitor has the formula:

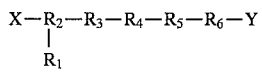

wherein X is hydrogen or is characterized by a backbone chain consisting of from 1 to 100 atoms; $R_1$ is selected from the group consisting of unsubstituted, mono-substituted, di-substituted and tri-substituted saturated homocyclic or heterocyclic ring structures; $R_2$ is a bond or is characterized by a backbone chain consisting of from 1 to 5 atoms; $R_3$ is a bond or is characterized by a backbone chain consisting of from 1 to 3 atoms; $R_4$ is any amino acid; $R_5$ is any L-amino acid which comprises a guanidinium- or amino-containing side chain group; $R_6$ is a non-amide bond; and Y is characterized by a backbone chain consisting of from 1 to 9 atoms. Examples of L-amino acids which comprise a guanidinium- or amino-containing side chains are arginine, lysine and ornithine.

Preferably, the saturated homocyclic or heterocyclic ring structure is supplied by a D-cyclohexyl-alanine (D-Cha), a mono-substituted D-Cha, a di-substituted D-Cha or a tri-substituted D-Cha residue (i.e., X is $H_2N$; $R_1$ is selected from the group consisting of unsubstituted, mono-substituted, di-substituted and tri-substituted cyclohexane; $R_2$ is $CH_2$-CH; and $R_3$ is C=O). Most preferably, X is HN; $R_1$ is cyclohexane; $R_2$ is $CH_2$—CH; $R_3$ is C=O; $R_4$ is proline; $R_5$ is arginine and Y is proline.

The presence of a non-amide bond at $R_6$ retards or prevents cleavage of the inhibitor by thrombin. The non-amide bond component may be formed by chemically modifying an amide bond. This may be achieved by methods well known in the art [M. Szelke et al., "Potent New Inhibitors of Human Renin" *Nature*, 299, pp. 555–57 (1982); D. H. Coy et al., "Facile Solid Phase Preparation of Proteins containing the $CH_2$—NH Peptide Bond Isostere and Application to the Synthesis of Somatostatin (SRIF) Octapeptide Analogues" *Peptides* 1986, D. Theodropoulos, Ed., Walter Gruyter & Co., Berlin, pp. 143–46 (1987)]. When a non-amide bond is formed in this manner, it is preferable that the chemical modification be performed prior to the addition of the portion of the molecule containing this bond to the rest of the thrombin inhibitor. In this manner, the portion containing this non-amide bond can be added en bloc, in a single synthesis step, to the rest of the inhibitor.

In the most preferred embodiment $R_5$ is Arg and Y is Pro. In this embodiment $R_6$ is a naturally occurring imide bond, which is slowly cleaved by thrombin. This avoids the necessity of pre-forming the non-amide bond and allows Y and $R_5$ to be added to the rest of the inhibitor sequentially rather than en bloc.

Further analysis of the Hirulog-8-thrombin crystallographic structure revealed that the proline bound to the D-Phe of Hirulog-8 was within 3.46 Å of the hydroxyl group of Tyr76 of thrombin. Because this distance was close enough to form hydrogen bonds, the substitution of an amino acid comprising a side chain group characterized by the capacity to accept a hydrogen bond at a pH of between about 5.5 and 9.5 for Pro at this position should increase the binding affinity of the inhibitor. Accordingly, another embodiment of this invention is a thrombin inhibitor of the formula:

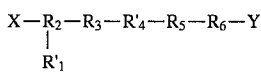

wherein $R_1'$ is selected from the group consisting of unsubstituted, mono-substituted, di-substituted and tri-substituted ring structures; $R_2$ is a bond or is characterized by a backbone chain consisting of from 1 to 5 atoms; $R_3$ is a bond or is characterized by a backbone chain consisting of from 1 to 3 atoms; $R_4'$ is any amino acid comprising a side chain group characterized by the capacity to accept a hydrogen bond at a pH of between about 5.5 and 9.5 ; $R_5$ is any L-amino acid which comprises a guanidinium- or amino-containing side chain group; $R_5$ is a non-amide bond; and Y is characterized by a backbone chain consisting of from 1 to 9 atoms.

Amino acids comprising a side chain group characterized by the capacity to accept a hydrogen bond at a pH of between about 5.5 and 9.5 are well known in the art. For example, histidine (which contains an imidazolium nitrogen), thioproline (which contains a thiol group) and isonipecotic acid (which contains a carboxylate side group) are each known to be hydrogen bond acceptors at pH 5.5 to 9.5.

More preferred thrombin inhibitors according to this embodiment comprise an unsubstituted, mono-substituted, di-substituted and tri-substituted cyclohexane at the $R_1'$ position. Most preferably X is $H_2N$, $R_1'$ is cyclohexane, $R_2$ is $CH_2$—CH=O and the resulting amino acid formed by X $R_1'$ $R_2'$ and $R_3$ is in the D-configuration (i.e., D-Cha)

In another preferred embodiment the thrombin inhibitor of this invention additionally consists of an anion binding exosite associating moiety (ABEAM), and a linker bound to Y at one end and the ABEAM at the other. Similar thrombin inhibitors have been described in U.S. Pat. No. 5,196,404, which is herein incorporated by reference, but the present preferred inhibitors are surprisingly and unexpectedly more potent.

In this embodiment, the linker region of the inhibitor provides a bridge between the CSDM and the ABEAM. Accordingly, it is the length of the linker, rather than its structure, that is of prime importance. The calculated length of the backbone chain which characterizes the linker must be at least about 18 Å—the distance between the catalytic site and the anion binding exosite of thrombin - and less than about 42 Å.

The backbone chain of the linker may comprise any atoms which are capable of bonding to at least two other atoms. Preferably, the backbone chain consists of any chemically feasible combination of atoms selected from oxygen, carbon, nitrogen and sulfur. Those of skill in the art are aware of what combination of the above backbone chain atoms falls within the required length based on known distances between various bonds [see, for example, R. T. Morrison and R. N. Boyd, *Organic Chemistry, 3rd Edition*, Allyn and Bacon, Inc., Boston, Mass. (1977)]. According to a preferred embodiment, the linker is a peptide which comprises the amino acid sequence Gly-Gly-Gly-Asn-Gly-Asp-Phe. Preferably, the amino acid bound to the ABEAM component is Phe.

The third domain of these preferred thrombin inhibitors is the ABEAM which binds to the anion binding exosite of thrombin. Preferably the ABEAM has the formula:

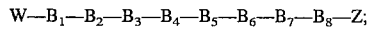

wherein W is a bond; $B_1$ is an anionic amino acid; $B_2$ is any amino acid; $B_3$ is Ile, Val, Leu, Nle or Phe; $B_4$ is Pro, Hyp, 3,4-dehydroPro, thiazolidine-4-carboxylate, Sar, any N-methyl amino acid or D-Ala; $B_5$ is an anionic amino acid; $B_6$ is an anionic amino acid; $B_7$ is a lipophilic amino acid selected from the group consisting of Tyr, Trp, Phe, Leu, Nle, Ile, Val, Cha, Pro, or a dipeptide consisting of one of these lipophilic amino acids and any amino acid; $B_8$ is a bond or a peptide containing from one to five residues of any amino acid; and Z is OH or is characterized by a backbone chain consisting of between 1 and 6 atoms.

Peptides which are homologous to the carboxy terminal portion of hirudin have been shown to bind to the anion binding exosite on thrombin [J. M. Maraganore et al., "Anticoagulant Activity of Synthetic Hirudin Peptides", *J. Biol. Chem.*, 264, pp. 8692–98 (1989); both of which is herein incorporated by reference].

According to a preferred embodiment of this invention, ABEAM is homologous to amino acids 56–64 of hirudin, i.e., $B_1$ is Glu; $B_2$ is Glu; $B_3$ is Ile; $B_4$ is Pro; $B_5$ is Glu; $B_6$ is Glu; By is Tyr-Leu, Tyr($SO_3H$)-Leu or Tyr ($OSO_3H$) -Leu, or (3-, 5-diiodoTyr) -Leu; $B_8$ is a bond; and Z is OH. It should be noted that native hirudin contains Tyr($OSO_3H$) at position 63. However, carboxy terminal hirudin peptides which contain Tyr($SO_3H$) have identical anticoagulant activity as those which contain the native Tyr($OSO_3H$) [see U.S. patent application Ser. No. 314,756, now abandoned].

Other ABEAM components within the scope of this invention may comprise those portions of any molecule known to bind to the anion binding site of thrombin. These include amino acids 1675–1686 of Factor V, amino acids 272–285 of platelet glycoprotein lb, amino acids 415–428 of thrombomodulin, amino acids 245–259 of prothrombin Fragment 2 and amino acids 30 to 44 of fibrinogen Aα chain. In addition, the ABEAM component may be selected from any of the hirudin peptide analogues described by J. L. Krstenansky et al., "Development of MDL-28,050, A Small Stable Antithrombin Agent Based On A Functional Domain of the Leech Protein, Hirudin", *Thromb. Haemostas.*, 63, pp. 208-14 (1990), particularly those comprising the sequence Asp-Tyr-Glu-Pro-Ile-Pro-Glu-Glu-Ala-Cha-(D-Glu).

The thrombin inhibitors of the present invention may be synthesized by various techniques which are well known in the art. These include organic chemical synthesis techniques, solid-phase peptide synthesis, solution-phase peptide synthesis or a combination of these techniques. Portions of some of the inhibitors of this invention may also be produced by other methods, such as enzymatic cleavage of natural or recombinant hirudin or recombinant DNA techniques. These portions may then be bound to the synthetically produced portions of the inhibitor to produce the final product according to this invention. The choice of synthesis technique will, of course, depend upon the composition of the particular inhibitor.

In a preferred embodiment of this invention, the thrombin inhibitor is synthesized via a mixed heterologous/solid phase technique. This technique involves the solid-phase synthesis of all or most of the peptide portion of the molecule, followed by the addition of the non-amino acid components which are synthesized by solution phase techniques. The non-amino acid may be coupled to the peptidic portion via solid-phase or solution-phase methods. Similarly, any remaining peptidic portions may also be added via solid-phase or solution phase methods. This constitutes the most cost-efficient procedures for producing commercial quantities of these molecules.

When "non-protein" amino acids are contained in the thrombin inhibitor of this invention, they may be either added directly to the growing chain during peptide synthesis or prepared by chemical modification of the complete synthesized peptide, depending on the nature of the desired "non-protein" amino acid. Those of skill in the chemical synthesis art are well aware of which "non-protein" amino acids may be added directly and which must be synthesized by chemically modifying the complete peptide chain following peptide synthesis.

The molecules of the present invention display potent anticoagulant activity. This activity may be assayed in vitro using any conventional technique. Preferably, an assay for anticoagulant activity involves direct determination of the thrombin-inhibitory activity of the molecule. Such techniques measure the inhibition of thrombin-catalyzed cleavage of colorimetric substrates or, more preferably, the increase in thrombin times or increase in activated partial thromboplastin times of human plasma. The latter assay measures factors in the "intrinsic" pathway of coagulation. Alternatively, the assay employed may use purified thrombin and fibrinogen to measure the inhibition of release of fibrinopeptides A or B by radioimmunoassay or ELISA.

The antiplatelet activity of the molecules of this invention may also be measured by any of a number of conventional platelet assays. Preferably, the assay will measure a change in the degree of aggregation of platelets or a change in the release of a platelet secretory component in the presence of thrombin. The former may be measured in an aggregometer. The latter may be measured using RIA or ELISA techniques specific for the secreted component.

The molecules of the present invention are useful in compositions, combinations and methods for the treatment and prophylaxis of various diseases attributed to thrombin-mediated and thrombin-associated functions and processes. These include myocardial infarction, stroke, pulmonary embolism, deep vein thrombosis, peripheral arterial occlusion, restenosis following arterial injury or invasive cardiological procedures, acute or chronic atherosclerosis, edema and inflammation, various cell regulatory processes (e.g. secretion, shape changes, proliferation), cancer and metastasis, and neurodegenerative diseases.

The thrombin inhibitors of the present invention may be formulated using conventional methods to prepare pharmaceutically useful compositions, such as the addition of a pharmaceutically acceptable carrier. These compositions and the methods employing them may be used for treating or preventing thrombotic diseases in a patient.

According to an alternate embodiment of the present invention, the thrombin inhibitors may be employed in combinations, compositions, and methods for treating thrombotic disease, and for decreasing the dosage of a thrombolytic agent required to establish reperfusion or prevent reocclusion in a patient. Additionally, the thrombin inhibitors of this invention may be used in combinations, compositions, and methods for decreasing reperfusion time or increasing reocclusion time in a patient treated with a thrombolytic agent. These combinations and compositions comprise a pharmaceutically effective amount of a thrombin inhibitor of the present invention and a pharmaceutically effective amount of a thrombolytic agent.

In these combinations and compositions, the thrombin inhibitor and the thrombolytic agent work in a complementary fashion to dissolve blood clots, resulting in decreased reperfusion times and increased reocclusion times in patients treated with them. Specifically, the thrombolytic agent dissolves the clot, while the thrombin inhibitor prevents newly exposed, clot-entrapped or clot-bound thrombin from regenerating the clot. The use of the thrombin inhibitor in the combinations and compositions of this invention advantageously allows the administration of a thrombolytic reagent in dosages previously considered too low to result in thrombolytic effects if given alone. This avoids some of the undesirable side effects associated with the use of thrombolytic agents, such as bleeding complications.

Thrombolytic agents which may be employed in the combinations and compositions of the present invention are those known in the art. Such agents include, but are not limited to, tissue plasminogen activator purified from natural sources, recombinant tissue plasminogen activator, streptokinase, urokinase, prourokinase, anisolated streptokinase plasminogen activator complex (ASPAC), animal salivary gland plasminogen activators and known, biologically active derivatives of any of the above.

The term "combination" as used herein, includes a single dosage form containing at least one thrombin inhibitor of this invention and at least one thrombolytic agent; a multiple dosage form, wherein the thrombin inhibitor and the thrombolytic agent are administered separately, but concurrently; or a multiple dosage form wherein the two components are administered separately, but sequentially. In sequential administration, the thrombin inhibitor may be given to the patient during the time period ranging from about 5 hours prior to about 5 hours after administration of the thrombolytic agent. Preferably, the thrombin inhibitor is administered to the patient during the period ranging from 2 hours prior to 2 hours following administration of the thrombolytic agent.

Alternatively, the thrombin inhibitor and the thrombolytic agent may be in the form of a single, conjugated molecule. Conjugation of the two components may be achieved by standard cross-linking techniques well known in the art. The single molecule may also take the form of a recombinant fusion protein, if both the thrombin inhibitor and the thrombolytic agent are peptidic.

Various dosage forms may be employed to administer the compositions and combinations of this invention. These include, but are not limited to, parenteral administration, oral administration and topical application. The compositions and combinations of this invention may be administered to the patient in any pharmaceutically acceptable dosage form, including those which may be administered to a patient intravenously as bolus or by continued infusion, intramuscularly—including paravertebrally and periarticularly—subcutaneously, intracutaneously, intra-articularly, intrasynovially, intrathecally, intra-lesionally, periostally or by oral, nasal, or topical routes. Such compositions and combinations are preferably adapted for topical, nasal, oral and parenteral administration, but, most preferably, are formulated for parenteral administration.

Parenteral compositions are most preferably administered intravenously either in a bolus form or as a constant infusion. If the thrombin inhibitor is being used as an antiplatelet compound, constant infusion is preferred. If the thrombin inhibitor is being used as an anticoagulant, a subcutaneous or intravenous bolus injection is preferred. For parenteral administration, fluid unit dose forms are prepared which contain a thrombin inhibitor of the present invention and a sterile vehicle. The thrombin inhibitor may be either suspended or dissolved, depending on the nature of the vehicle and the nature of the particular thrombin inhibitor. Parenteral compositions are normally prepared by dissolving the thrombin inhibitor in a vehicle, optionally together with other components, and filter sterilizing before filling into a suitable vial or ampule and sealing. Preferably, adjuvants such as a local anesthetic, preservatives and buffering agents are also dissolved in the vehicle. The composition may then be frozen and lyophilized to enhance stability.

Parenteral suspensions are prepared in substantially the same manner, except that the active component is suspended rather than dissolved in the vehicle. Sterilization of the compositions is preferably achieved by exposure to ethylene oxide before suspension in the sterile vehicle. Advantageously, a surfactant or wetting agent is included in the composition to facilitate uniform distribution of its components.

Tablets and capsules for oral administration may contain conventional excipients, such as binding agents, fillers, diluents, tableting agents, lubricants, disintegrants, and wetting agents. The tablet may be coated according to methods well known in the art. Suitable fillers which may be employed include cellulose, mannitol, lactose and other similar agents. Suitable disintegrants include, but are not limited to, starch, polyvinylpyrrolidone and starch derivatives, such as sodium starch glycolate. Suitable lubricants include, for example, magnesium stearate. Suitable wetting agents include sodium lauryl sulfate.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives. These include suspending agents; such as sorbitol, syrup, methyl cellulose, gelatin, hydroxyethylcellulose, carboxymethylcellulose, aluminum stearate gel or hydrogenated edible fats; emulsifying agents which include lecithin, sorbitan monooleate, polyethylene glycols, or acacia; non-aqueous vehicles, such as almond oil, fractionated coconut oil, and oily esters; and preservatives, such as methyl or propyl p-hydroxybenzoate or sorbic acid.

Compositions formulated for topical administration may, for example, be in aqueous jelly, oily suspension or emulsified ointment form.

The dosage and dose rate of the thrombin inhibitor will depend on a variety of factors, such as the size of the patient, the specific pharmaceutical composition used, the object of the treatment, i.e., therapy or prophylaxis, the nature of the thrombotic disease to be treated, and the judgment of the treating physician.

According to the present invention, a preferred pharmaceutically effective daily dose of the thrombin inhibitor of this invention is between about 0.5 nmoles/kg body weight of the patient to be treated ("body weight") and about 2.5 μmoles/kg body weight. In combinations containing a thrombolytic agent, a pharmaceutically effective daily dose of the thrombolytic is between about 10% and 80% of the conventional dosage range. The "conventional dosage range" of a thrombolytic agent is the daily dosage used when that agent is employed in a monotherapy. [*Physician's Desk Reference* 1989, 43rd Edition, Edward R. Barnhart, publisher]. That conventional dosage range will, of course, vary depending on the thrombolytic agent employed. Examples of conventional dosage ranges are as follows: urokinase - 500,000 to 6,250,000 units/patient; streptokinase - 140,000 to 2,500,000 units/patient; tPA—0.5 to 5.0 mg/kg body weight; ASPAC - 0.1 to 10 units/kg body weight.

Most preferably, the therapeutic and prophylactic compositions of the present invention comprise a dosage of between about 5 nmoles/kg body weight and about 250 nmoles/kg body weight of the thrombin inhibitor. Most preferred combinations comprise the same amount of the thrombin inhibitor and between about 10% and about 70% of the conventional dosage range of a thrombolytic agent. It should also be understood that a daily pharmaceutically effective dose of either the thrombin inhibitors of this invention or the thrombolytic agent present in combinations of the invention, may be less than or greater than the specific ranges cited above.

Once improvement in the patient's condition has occurred, a maintenance dose of a combination or composition of this invention is administered, if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment upon any recurrence of disease symptoms.

According to an alternate embodiment of this invention, thrombin inhibitors may be used in compositions and methods for coating the surfaces of invasive devices, resulting in a lower risk of clot formation or platelet activation in patients receiving such devices. Surfaces that may be coated with the compositions of this invention include, for example, prostheses, artificial valves, vascular grafts, stents and catheters. Methods and compositions for coating these devices are known to those of skill in the art. These include chemical cross-linking or physical adsorption of the thrombin inhibitor-containing compositions to the surfaces of the devices.

According to a further embodiment of the present invention, thrombin inhibitors may be used for ex vivo thrombus imaging in a patient. The term "ex vivo thrombus imaging", as used herein, refers to viewing, outside the human body, a blood clot in a patient. As explained below, this is achieved through the use of a radioactively labelled thrombin inhibitor which is administered to the patient and an external device that detects radioactivity and converts it to an image. In this embodiment, the thrombin inhibitor is labelled with a radioisotope. The choice of radioisotope is based upon a number of well-known factors, for example, toxicity, biological half-life and detectability. Preferred radioisotopes include, but are not limited to, $^{125}$I, $^{123}$I and $^{111}$In. Techniques for labelling the thrombin inhibitor are well known in the art. Most preferably, the radioisotope is $^{123}$I and the labelling is achieved using $^{123}$I-Bolton-Hunter Reagent. The labelled thrombin inhibitor is administered to a patient and allowed to bind to the thrombin contained in a clot. The clot is then observed by utilizing well-known detecting means, such as a camera capable of detecting radioactivity coupled to a computer imaging system. This technique also yields images of platelet-bound thrombin and meizothrombin.

This invention also relates to compositions containing the thrombin inhibitors of this invention and methods for using such compositions in the treatment of tumor metastases. The efficacy of the thrombin inhibitors of this invention for the treatment of tumor metastases is manifested by the inhibition of metastatic growth. This is based upon the presence of a procoagulant enzyme in certain cancer cells. This enzyme activates the conversion of Factor X to Factor Xa in the coagulation cascade, resulting in fibrin deposition which, in turn, serves as a substrate for tumor growth. By inhibiting fibrin deposition through the inhibition of thrombin, the molecules of the present invention serve as effective anti-metastatic tumor agents. Examples of metastatic tumors which may be treated by the thrombin inhibitors of this invention include, but are not limited to, carcinoma of the brain, carcinoma of the liver, carcinoma of the lung, osteocarcinoma and neoplastic plasma cell carcinoma.

The invention also relates to methods and compositions employing the above-described thrombin inhibitors to inhibit thrombin-induced endothelial cell activation. This inhibition includes the repression of platelet activation factor (PAF) synthesis by endothelial cells. These compositions and methods have important applications in the treatment of diseases characterized by thrombin-induced inflammation and edema, which is thought to be mediated by PAF. Such diseases include, but are not limited to, adult respiratory distress syndrome, septic shock, septicemia and reperfusion damage.

Early stages of septic shock include discrete, acute inflammatory and coagulopathic responses. It has previously been shown that injection of baboons with a lethal dose of live *E. coli* leads to marked declines in neutrophil count, blood pressure and hematocrit. Changes in blood pressure and hematocrit are due in part to the generation of a disseminated intravascular coagulopathy (DIC) and have been shown to parallel consumption of fibrinogen [F. B. Taylor et al., "Protein C Prevents the Coagulopathic and Lethal Effects of *Escherichia coli* Infusion in the Baboon", *J. Clin. Invest.*, 79, pp. 918–25 (1987)]. Neutropenia is due to the severe inflammatory response caused by septic shock which results in marked increases in tumor necrosis factor levels. The thrombin inhibitors of this invention may be utilized in compositions and methods for treating or preventing DIC in septicemia and other diseases.

This invention also relates to the use of the above-described thrombin inhibitors, or compositions comprising them, as anticoagulants for extracorporeal blood. As used herein, the term "extracorporeal blood" includes blood removed in line from a patient, subjected to extracorporeal treatment, and then returned to the patient in such processes as dialysis procedures, blood filtration, or blood bypass during surgery. The term also includes blood products which are stored extracorporeally for eventual administration to a patient and blood collected from a patient to be used for various assays. Such products include whole blood, plasma, or any blood fraction in which inhibition of coagulation is desired.

The amount or concentration of thrombin inhibitor in these types of compositions is based on the volume of blood to be treated or, more preferably, its thrombin content. Preferably, an effective amount of a thrombin inhibitor of this invention for preventing coagulation in extracorporeal blood is from about 0.5 nmoles/60 ml of extracorporeal blood to about 2.5 μmoles/60 ml of extracorporeal blood.

The thrombin inhibitors of this invention may also be used to inhibit clot-bound thrombin, which is believed to contribute to clot accretion. This is particularly important because commonly used anti-thrombin agents, such as heparin and low molecular weight heparin, are ineffective against clot-bound thrombin.

Finally, the thrombin inhibitors of this invention may be employed in compositions and methods for treating neurodegenerative diseases. Thrombin is known to cause neurite retraction, a process suggestive of the rounding in shape changes of brain cells and implicated in neurodegenerative diseases, such as Alzheimer's disease and Parkinson's disease.

In order that the invention described herein may be more fully understood, the following examples are set forth. It should be understood that these examples are for illustrative purposes only and are not to be construed as limiting this invention in any manner.

EXAMPLE 1

Design Of A Thrombin Inhibitor Capable Of Blocking The Catalytic Site And Binding To The Anion Binding Exosite Carboxy terminal hirudin peptides effectively block thrombin-catalyzed fibrinogen hydrolysis, but not chromogenic substrate hydrolysis [J. M. Maraganore et al., *J. Biol. Chem.*, 264, pp. 8692–98 (1989)]. In addition, hirudin peptides do not neutralize thrombin-catalyzed activation of Factors V and VIII [J. W. Fenton, II, et al., "Hirudin Inhibition by Thrombin", *Anglo. Archiv. Biol.*, (1989)].

Hirudin peptides, such as $Tyr_{63}$-O-sulfate-N-acetyl-hirudins$_{53-64}$ ("hirugen"), exhibit potent inhibitory effects toward thrombin-induced platelet activation in vitro [J. A. Jakubowski and J. M. Maragenore, "Inhibition of Thrombin-Induced Platelet Activities By A Synthetic 12 Amino Acid Residue Sulfated Peptide (Hirugen)", *Blood*, p. 1213 (1989)]. Nevertheless, a thrombin inhibitor capable of blocking the active site may be required for inhibition of platelet thrombosis in vivo, if activation of Factors V and VIII are critical and rate-limiting steps. This conclusion is warranted from results obtained with the irreversible thrombin inhibitor (D-Phe)-Pro-Arg-$CH_2Cl$ [S. R. Hanson and L. A. Harker, "Interruption of Acute Platelet-Dependent Thrombosis by the Synthetic Antithrombin D-Phenylalanyl-L-Prolyl-L-Arginyl Chloromethyl Ketone", *Proc. Natl. Acad. Sci. USA*, 85, pp. 3184–88 (1988)]and other reversible thrombin inhibitors [J. F. Eidt et al., "Thrombin is an Important Mediator of Platelet Aggregation in Stenosed Canine Coronary Arteries with Endothelial Injury", *J. Clin. Invest.*, 84, pp. 18–27 (1989)].

Using the above knowledge that the $NH_2$-terminus of hirudin peptides is proximal to Lys-149, we employed a three-dimensional model of thrombin [B. Furie, et al., "Computer-Generated Models of Blood Coagulation Factor Xa, Factor IXa, and Thrombin Based Upon Structural Homology with Other Serine Proteases", *J. Biol. Chem.*, 257, pp. 3875–82 (1982)] to design an agent which: 1) binds to the anion binding exosite of thrombin; and, 2) is capable of blocking the active site pocket of thrombin and inhibiting the function of catalytic residues contained therein.

We determined that the minimal distance from the $\epsilon$-$NH_2$ of Lys-149 to the $\beta$-hydroxylate of Ser-195 is 18–20 Å. Based on a 3 Å/amino acid residue length, we calculated that at least about 4–7 amino acids would be required to link a hirudin peptide, such as $Tyr_{63}$-O- sulfate-hirudin$_{53-64}$, to a domain comprising an active-site inhibitor structure. The composition of the linker was designed to be glycine. Glycine was chosen in order to engineer the greatest flexibility of a linker for these preliminary investigations. It should be understood, however, that other, more rigid biopolymer linkers may also be employed.

We chose the sequence (D-Phe)-Pro-Arg-Pro as the active site inhibitor because thrombin exhibits specificity for Arg as the $P_1$ amino acid in the cleavage of substrates. A Pro following the Arg (the $P_1'$ amino acid) yields a bond that is cleaved very slowly by thrombin. We designed alternate peptides by replacing that Pro with a sarcosyl- or N-methylalanine amino acid or by chemical reduction of an Arg-Gly scissile bond.

EXAMPLE 2

Synthesis Of Hirulog-8

Hirulog-8 has the formula: H-(D-Phe)-Pro-Arg-Pro-(Gly)$_4$-Asn-Gly-Asp-Phe-Glu-Glu-Ile-Pro-Glu-Glu-Tyr-Leu-OH. We synthesized Hirulog-8 by conventional solid-phase peptide synthesis employing an Applied Biosystems 430 A Peptide Synthesizer. This peptide was synthesized using BOC-L-Leucine-O-divinylbenzene resin. Additional t-BOC-amino acids (Peninsula Laboratories, Belmont, Calif.) used included BOC-O-2,6-dichlorobenzyl tyrosine, BOC-L-glutamic acid ($\gamma$-benzyl ester), BOC-L-proline, BOC-L-isoleucine, BOC-L-phenylalanine, BOC-L-aspartic acid ($\beta$-benzyl ester), BOC-glycine, BOC-L-asparagine, BOC-D-phenylalanine, and BOC-L-arginine. In order to achieve higher yields in synthesis, the (Gly)$_4$ linker segment was attached in two cycles of manual addition of BOC-glycylglycine (Beckman Biosciences, Inc., Philadelphia, Pa.). After completion of synthesis, the peptide was fully deprotected and uncoupled from the divinylbenzene resin by treatment with anhydrous HF: R-cresol: ethylmethyl sulfate (10:1:1 , v/v/v). Following removal from the resin, the peptide was lyophilized to dryness.

Crude Hirulog-8 was purified by reverse-phase HPLC employing an Applied Biosystems 151A liquid chromatographic system and a Vydac $C_{18}$ column (2.2×25 cm). The column was equilibrated in 0.1% TFA/water and developed with a linear gradient of increasing acetonitrile concentration from 0 to 80% over 45 minutes in the 0. 1% TFA at a flow-rate of 4.0 ml/min. The effluent stream was monitored for absorbance at 229 nm and fractions were collected manually. We purified 25–30 mg of crude Hirulog-8 by HPLC and recovered 15–20 mg of pure peptide.

We confirmed the structure of purified Hirulog-8 by amino acid and sequence analyses. Amino acid hydrolysates were prepared by treating the peptide with 6 N HCl, in vacuo, at 110° C. for 24 hrs. We then analyzed the hydrolysates by ion-exchange chromatography and subsequent ninhydrin derivatization/detection using a Beckman 6300 automated analyzer. We performed sequence analysis using automated Edman degradation on an Applied Biosystems 470A gas-phase sequencer equipped with a Model 900A data system. Phenylthiohydantoin (PTH) amino acids were analyzed on-line using an Applied Biosystems 120A PTH-analyzer and a PTH-$C_{18}$ column (2.1×220 mm).

EXAMPLE 3

Design Of 1 - And 2-Position

Substituted Hirulogs

We obtained the X-ray crystallographic structure of the Hirulog-8: thrombin complex by the following steps. First, we generated Hirulog-8:thrombin complex crystals of suitable quality to obtain a high resolution diffraction pattern. We next collected diffractometer data employing these crystals. Finally, we determined the 3-dimensional structure of the Hirulog-8:thrombin complex using molecular replacement rotation/translation methods employing the coordinates of the PPACK:thrombin [W. Bode et al., "The Refined 1.9 Å Crystal Structure of Human $\alpha$-Thrombin: Interaction With D-Phe-Pro-Arg-Chloromethylketone and Significance of the Tyr-Pro-Pro-Trp Insertion Segment", *EMBO J.*, 8, pp. 3467–75 (1989)]and hirudin:thrombin [T. J. Rydel et al., "The Structure of a Complex of Recombinant Hirudin and Human $\alpha$-Thrombin", *Science*, 49, pp. 277–80, (1990)] complexes. As shown in FIG. 1, the structure of Hirulog-8 bound to thrombin was resolved allowing resolution of the D-Phe-Pro-Arg sequence of the CSDM and the Asp-Phe-Glu-Glu-Ile segment of the ABEAM.

In FIG. 1, thrombin is displayed in white, except for its active site, which is shown in dense dots. Hirulog-8 is depicted in sparse dots. The left-hand portion of Hirulog-8 nearest the thrombin active site is the CSDM. The right-hand portion is the ABEAM. Other amino acids of Hirulog-8 are not shown in Figure 1 because electron densities corresponding to them could not be assigned.

Figure 2:
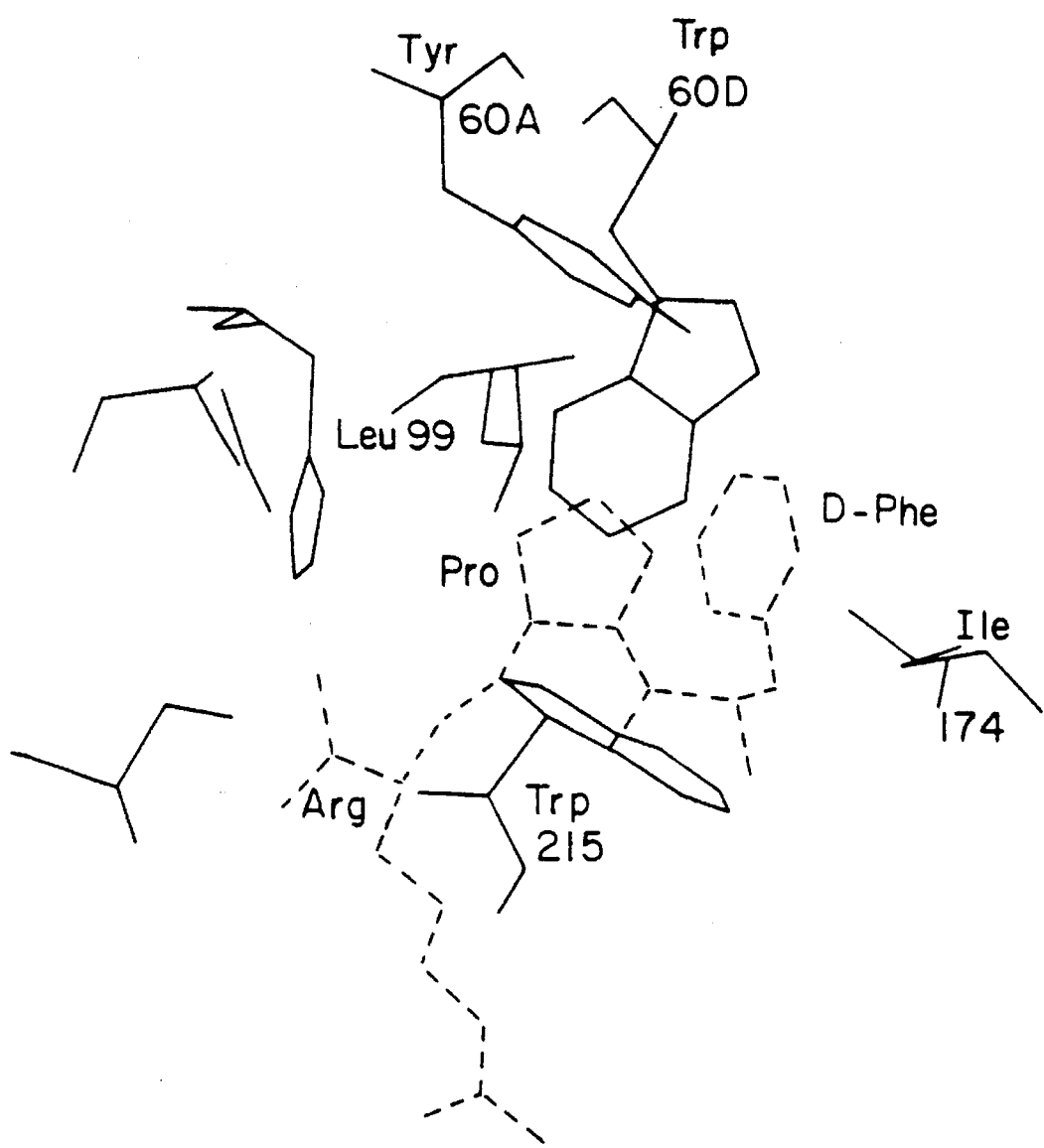
FIG. 2 is a schematic depiction of the interaction between the 1-position D-Phe and the 2-postion proline of Hirulog-8 and the hydrophobic pocket adjacent the catalytic site of thrombin.

Examination of the ABEAM portion of the Hirulog-8:thrombin structure showed the positioning of the 1-position amino acid (D-Phe) in a hydrophobic pocket formed by His57, Tyr60A, Trp60D, Leu99, Ile174, and Trp215 of thrombin. The D-Phe residue formed close van der Waals contacts with Leu99, Ile174, and Trp215 (FIG. 2). In FIG. 2, thrombin is displayed in soid lines and Hirulog-8 is in dashed lines. The positioning of the D-Phe residue within the pocket suggested that substitutions at the 1-position which enhance lipophilic contacts would lead to an increased binding affinity of the CSDM moiety in the thrombin inhibitors of this invention. Accordingly, we replaced the D-Phe residue of Hirulog-8 with either D-napthylalanine (D-NPA) or D-cyclohexylalanine (D-Cha) to form D-NPA-Hirulog-8 and D-Cha-Hirulog-8, respectively.

The binding of the CSDM of Hirulog-8 to the catalytic site of thrombin was also found to include apolar interactions between the first proline of the inhibitor (adjacent to D-Phe) and a pocket defined by His57, Tyr60A and Trp60D of thrombin (FIG. 2). Furthermore, that proline was found to be within 3.46 Å of the phenolic hydroxyl group of thrombin Tyr60A (FIG. 2). In FIG. 2, thrombin is depicted in solid lines and Hirulog-8 in dashed lines.

The proximity of this proline to Tyr60A of thrombin suggested the potential for hydrogen bond formation between the two. By substituting proline with an amino acid capable of forming hydrogen bonds, the stability of the CSDM binding to the thrombin active site can be increased. This, in turn, would increase the inhibitory activity of such a molecule. Therefore, we replaced the proline of Hirulog-8 with either L-histidine ($His_2$-Hirulog-8), L-thioproline ($TPro_2$-Hirulog-8) or isonipecotic acid ($Inp_2$-Hirulog-$_8$). Each of these substitutions created a hydrogen bond acceptor at the 2-position ($R_4'$ component) of the thrombin inhibitors of this invention (i.e., an imidazolium nitrogen, a thiol and a carboxylate, respectively).

EXAMPLE 4

Synthesis of 1-Position Substituted Hirulogs

D-Npa-Hirulog-8 was synthesized in the same manner as Hirulog-8 (Example 2), except that Boc-D-napthylalanine (Bachem Inc., Torrance, Calif.) was employed in place of D-Phe at the last cycle of synthesis. D-Cha-Hirulog-8 was similarly prepared using Boc-D-cyclohexylalanine (Bachem Biosciences, Pa.) at the last cycle of synthesis.

Both 1-position substituted peptides were purified as described for Hirulog-8 in Example 2. The purified peptides were characterized by amino acid analysis and by FAB-MS.

EXAMPLE 5

Synthesis of 2-Position Substituted Hirulog Derivatives

Substitutions at the 2-position were designed having the formula: (D-Cha)-X-Arg-HPro- (Gly)$_4$-Asn-Gly-Asp-Phe-Glu-Glu-Ile-Pro-Glu-Glu-Tyr-Leu or (D-Phe)-X-Arg-HPro-(Gly)$_4$-Asn-Gly-Asp-Phe-Glu-Glu-Ile-Pro-Glu-Glu-Tyr-Leu, wherein X is either histidine, thioproline or isonipecotic acid. These peptides are synthesized essentially as described in Example 2 and Example 4 except for incorporation of Boc-L-hydroxyproline (Bachem, Inc.) instead of Boc-L-proline at cycle 16 of the synthesis and either Boc-N-im-CBZ-L-histidine, Boc-L-thioproline, or Boc-isonipecotic acid (all obtained from Bachem, Inc.) instead of Boc-L-proline at cycle 18. HPro is used at the 4-position to slow down the rate of cleavage of the inhibitor by thrombin. The peptides are purified and characterized as described in Example 2.

EXAMPLE 6

Characterization Of Antithrombin Activities Of 1-Position Substituted Hirulogs

We compared the inhibition of thrombincatalyzed hydrolysis of Spectrozyme TH (tosyl-Gly-Pro-Arg-p-nitroanilide; American Diagnostica, New York, N.Y.) of Hirulog-8, D-Cha-Hirulog-8 and D-Npa-Hirulog-8 in an assay. Specifically, we measured the initial rate velocities in the presence or absence of each inhibitor over a range of substrate concentrations from 2.2 to 22 µM. The thrombincatalyzed rate was monitored in a Cary 19 spectrophotometer at 405 nm and recorded continuously as a function of time. Kinetics were performed at room temperature (25±1° C.) in a 0.05 M sodium borate buffer, pH 8.4, containing 0.1M NaCl.

For a typical enzyme reaction, 1.0 ml of buffer was added to both the sample and reference cuvettes. Thrombin (3.2× $10^{-9}$M, final concentration) and the hirulog (0–4×$10^{-8}$M) were added to the sample cuvette prior to addition of Spectrozyme TH (2.2–22µM). Immediately following addition of substrate, the contents of the sample cuvette were mixed by use of a plastic pipette. The reaction was monitored spectrophotometrically for 5–15 minutes.

Initial rate velocities at each substrate concentration were expressed as moles Spectrozyme TH hydrolyzed/sec/mole thrombin. This was determined during the initial linear phase of the reaction (≦15% total hydrolysis of substrate) by measuring the slope of the hydrolytic reaction. Lineweaver-Burke plots were constructed accordingly, by plotting the inverse of the initial velocity against the inverse of the substrate concentration. Shown below are the inhibitory constants obtained for Hirulog-8 and derivatives of the present invention.

| Derivative | $K_i$, nM |
| --- | --- |
| Hirulog-8 | 1.4 |
| D-Cha-Hirulog-8 | 0.12 |
| D-Npa-Hirulog-8 | 4.3 |

As can be seen from these results, substitution of D-Phe in Hirulog-8 with D-Cha results in a surprising and unexpected decrease in $K_i$ by one order of magnitude. This finding indicates that substitution of D-Phe by D-Cha increases the binding affinity of the CSDM in the inhibitors of this invention. The failure of D-Npa-Hirulog-8 to decrease $K_i$ indicates that the presence of a saturated ring structure at this position causes the increased binding affinity. D-Cha contains such a saturated ring, while D-Npa contains an unsaturated ring.

Molecules containing the 2-position substitutions described in Example 5 will display similar surprising and unexpected decreases in $K_i$.

EXAMPLE 7

Anticoagulant Activity Of $A_1$-Substituted Hirulogs

We compared the anticoagulant activity of $Tyr_{63}$-O-sulfate-N-acetyl-hirudin$_{53-64}$ ("hirugen"), recombinant hirudin (American Diagnostica), Hirulog-8, and the 1-position substituted hirulogs of the present invention using pooled, normal human plasma (George King Biomedical, Overland Park, Kans.) and a Coag-A-Mate XC instrument (General Diagnostics, Organon Technica, Oklahoma City, Okla.). Activity was monitored using the activated partial thromboplastin time (APTT) assay with $CaCl_2$ and phospholipid solutions obtained from the manufacturer. Recombinant hirudin (American Diagnostica), Hirulog-8, D-Cha-Hirulog-8 or hirugen was then added to the APTT determination wells at a final concentrations of 10 to 32,300 ng/ml in a total volume of 25 µl prior to addition of 100 µl of plasma.

Figure 3:
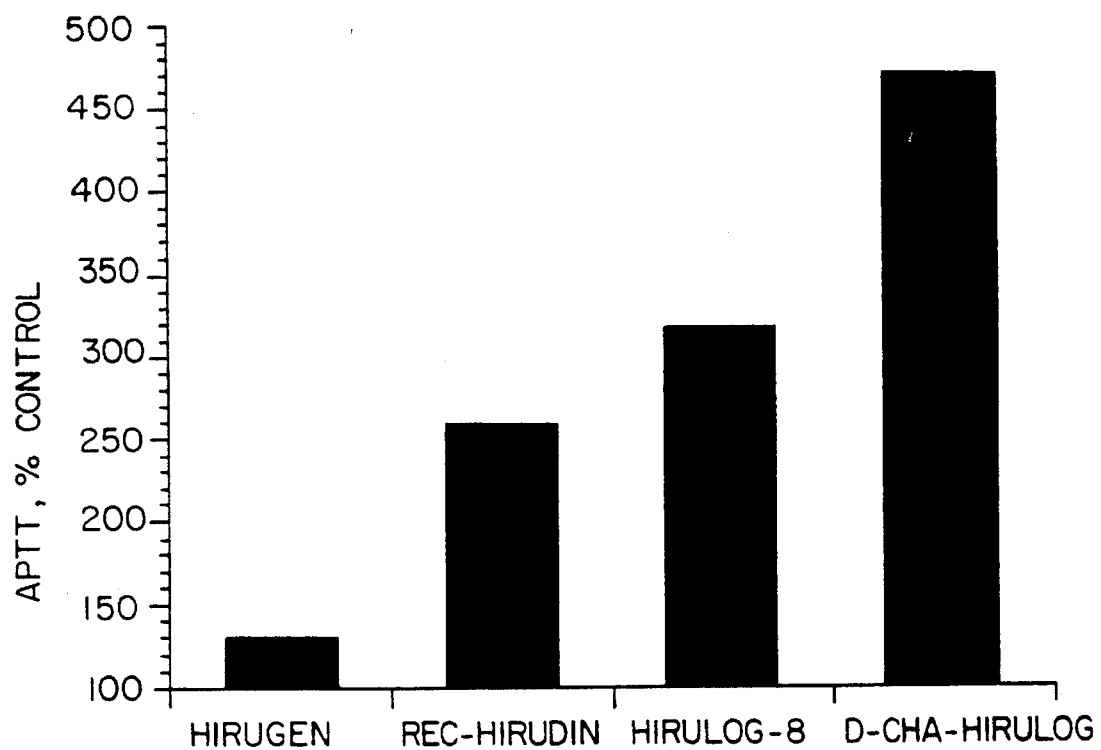
FIG. 3 depicts the comparative anticoagulant activity of hirugen, recombinant hirudin, Hirulog-8 and D-Cha-hirulog.

As shown in FIG. 3, D-Cha-Hirulog-8 prolonged APTT to 470% of control values at a concentration of 1 µg/µl. This increase was significantly greater than the increases in APTT caused by hirugen, recombinant hirudin or Hirulog-8 at the same concentration. Thus, in addition to showing enhanced antithrombin activities in vitro over Hirulog-8, D-Cha-Hirulog-8 also showed a significantly increased anticoagulant effect in plasma assays over Hirulog-8.

Molecules containing the 2-position substitutions described in Example 5 will display increases in APTT that are greater than Hirulog-8.

While we have hereinbefore presented a number of embodiments of this invention, it is apparent that our basic construction can be altered to provide other embodiments which utilize the molecules, compositions, combinations and methods of this invention. Therefore, it will be appreciated that the scope of this invention is to be defined by the claims appended hereto rather than the specific embodiments which have been presented hereinbefore by way of example.

We claim:

1. A method for coating the surface of an invasive device to be inserted into a patient, said method comprising the step of contacting said surface with a composition comprising:

(a) a catalytic site-directed thrombin inhibitor characterized by the formula:

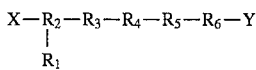

wherein X is HN; $R_1$ is cyclohexyl; $R_2$ is $CH_2$—12 CH; $R_3$ is C=O; $R_4$ is Pro or any amino acid comprising a side chain group characterized by the capacity to accept a hydrogen bond at a pH of between 5.5 and 9.5; $R_5$ is any L-amino acid which comprises a guanidinium- or amino-containing side chain group; $R_6$ is a non-amide bond that retards or prevents the cleavage of said inhibitor by thrombin; and Y is selected from the group consisting of sarcosine, N-methyl alanine, hydroxyproline and any naturally occurring L-α-amino acid; and the amino acid defined by components X, $R_1$, $R_2$, and $R_3$ is in the D configuration; and (b) a suitable buffer.

2. A method for coating the surface of an invasive device to be inserted into a patient, said method comprising the step of contacting said surface with a composition comprising:

(a) a thormbin inhibitor consisting of:

i) a catalytic site directed moiety (CSDM) of the formula:

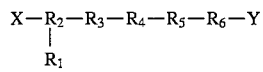

wherein X is hydrogen or is characterized by a backbone chain consisting of from 1 to 100 atoms; $R_1$ is selected from the group consisting of unsubstituted, mono-substituted, di-substituted and tri-substituted saturated homocyclic or heterocyclic ring structures; $R_2$ is a bond or is characterized by a backbone chain consisting of from 1 to 5 atoms; $R_3$ is a bond or is characterized by a backbone chain consisting of from 1 to 3 atoms; $R_4$ is any amino acid; $R_5$ is any L-amino acid which comprises a guanidinium- or amino-containing side chain group; $R_6$ is a non-amide bond; and Y is characterized by a backbone chain consisting of from 1 to 9 atoms;

ii) a linker moiety bonded to Y, said linker moiety characterized by a backbone chain having a calculated length of between 18 Å and 42 Å; and iii) an anion binding exosite associating moiety, said catalytic site-directed moiety being bound to said linker moiety and said linker moiety being bound to said anion binding exosite associating moiety; wherein said inhibitor is capable of simultaneously binding to the catalytic site and the anion binding exosite of thrombin; and (b) a suitable buffer.

3. The method according to claim 1 or 2, wherein said thrombin inhibitor comprises the amino acid sequence:

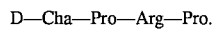

4. The method according to claim 1 or 2, wherein $R_4$ is selected from the group consisting of histidine, thioproline and isonipecotic acid.

5. The method according to claim 1 or 2, wherein said patient is a human.

6. The method according to claim 2, wherein said anion binding exosite associating moiety consists of the formula:

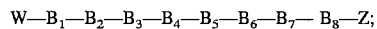

wherein W is a bond; $B_1$ is an anionic amino acid; $B_2$ is any amino acid; $B_3$ is Ile, Val, Leu, Nle or Phe; $B_4$ is Pro, Hyp, 3,4-dehydroPro, thiazolidine-4-carboxylate, Sar, any N-methyl amino acid or D-Ala; $B_5$ is an anionic amino acid; $B_6$ is an anionic amino acid; $B_7$ is a lipophilic amino acid selected from the group consisting of Tyr, Trp, Phe, Leu, Nle, Ile, Val, Cha, Pro, or a dipeptide consisting of one of said lipophilic amino acids and any amino acid; $B_8$ is a bond or a peptide containing from one to five independently selected residues of any amino acid; and Z is OH or is characterized by a backbone chain consisting of from 1 to 6 atoms.

7. The method according to claim 6, wherein $B_1$ is Glu; $B_2$ is Glu; $B_3$ is Ile; $B_4$ is Pro; $B_5$ is Glu; $B_6$ is Glu; $B_7$ is Tyr-Leu, Tyr($SO_3H$)-Leu, Tyr($OSO_3H$)-Leu or (3-, 5-diiodoTyr)-Leu; $B_8$ is a bond; and Z is OH.

8. The method according to claim 2, wherein said backbone chain of said linker moiety consists of any combination of atoms selected from the group consisting of carbon, nitrogen, sulfur and oxygen.

9. The method according to claim 8, wherein said linker comprises the amino acid sequence: Gly-Gly-Gly-Asn-Gly-Asp-Phe.

10. The method according to claim 2, wherein said thrombin inhibitor is D-Cha-Hirulog-8.

11. The method according to claim 2, wherein X is $H_2N$; $R_1$ is selected from the group consisting of unsubstituted, monosubstituted, disubstituted and trisubstituted cyclohexyl; $R_2$ is $CH_2$—CH; and $R_3$ is C=O.

* * * * *